US008323237B2

(12) United States Patent
Radmer et al.

(10) Patent No.: US 8,323,237 B2
(45) Date of Patent: Dec. 4, 2012

(54) ONE-HAND OPERATED DRUG MIXING AND EXPELLING DEVICE

(75) Inventors: Bo Radmer, Hilleroed (DK); Morten Revsgaard Frederiksen, Copenhagen K (DK)

(73) Assignee: Novo Nordisk HealthCare AG, Zurich (CH)

( * ) Notice: Subject to any disclaimer, the term of this patent is extended or adjusted under 35 U.S.C. 154(b) by 127 days.

(21) Appl. No.: 12/304,590

(22) PCT Filed: Jun. 7, 2007

(86) PCT No.: PCT/EP2007/055623
§ 371 (c)(1),
(2), (4) Date: Mar. 5, 2009

(87) PCT Pub. No.: WO2007/147741
PCT Pub. Date: Dec. 27, 2007

(65) Prior Publication Data

US 2009/0204066 A1 Aug. 13, 2009

Related U.S. Application Data

(60) Provisional application No. 60/816,049, filed on Jun. 23, 2006, provisional application No. 60/839,283, filed on Aug. 22, 2006.

(30) Foreign Application Priority Data

Jun. 21, 2006 (EP) .................................... 06115841
Aug. 18, 2006 (EP) .................................... 06119143

(51) Int. Cl.
*A61M 37/00* (2006.01)
*A61M 5/32* (2006.01)
*A61B 19/00* (2006.01)

(52) U.S. Cl. ............... 604/89; 604/92; 604/86; 604/416

(58) Field of Classification Search .................... 604/83, 604/87, 89–92
See application file for complete search history.

(56) References Cited

U.S. PATENT DOCUMENTS 3,570,486 A 3/1971 Engelsher et al.
(Continued)

FOREIGN PATENT DOCUMENTS

DE 4314090 11/1994
(Continued)

OTHER PUBLICATIONS

English Language Abstract of French Patent No. 2714824, published Jul. 13, 1995.

(Continued)

*Primary Examiner* — Nicholas Lucchesi
*Assistant Examiner* — Rebecca E Eisenberg
(74) *Attorney, Agent, or Firm* — Wesley A. Nicolas; Marc A. Began; Reza Green

(57) ABSTRACT

A drug mixing and expelling device (1) for mixing a drug with a liquid, thereby forming a reconstituted liquid drug. The device comprises a reservoir (2) containing a liquid, a vial (4) containing a drug, a vial, means (5) for establishing a fluid connection between the reservoir and a vial positioned in the vial adapter (3), means (7, 8) for forcing the liquid from the reservoir to a vial, and means (9) for activating said forcing means during establishment of the fluid connection between the reservoir and the vial. The forcing of liquid into the vial provides a pressure therein, which can be used for infusion of the reconstituted drug directly from the vial. The device also comprises a suction unit (13) for aspiration.

20 Claims, 6 Drawing Sheets

U.S. PATENT DOCUMENTS

| | | | | |
|---|---|---|---|---|
| 3,636,950 | A | | 1/1972 | Gomez et al. |
| 3,882,909 | A | | 5/1975 | Ogle |
| 4,410,321 | A | | 10/1983 | Pearson et al. |
| 4,689,042 | A | | 8/1987 | Sarnoff et al. |
| 4,738,660 | A | | 4/1988 | Lucas |
| 4,755,169 | A | * | 7/1988 | Sarnoff et al. ................ 604/511 |
| 4,861,335 | A | | 8/1989 | Reynolds |
| 5,037,390 | A | | 8/1991 | Raines et al. |
| 5,281,198 | A | | 1/1994 | Haber et al. |
| 5,329,976 | A | | 7/1994 | Haber et al. |
| 5,336,180 | A | | 8/1994 | Kriesel et al. |
| 5,419,771 | A | | 5/1995 | Kriesel |
| 5,460,204 | A | | 10/1995 | Rossi |
| 5,569,191 | A | | 10/1996 | Meyer |
| 6,508,791 | B1 | | 1/2003 | Guerrero |
| 6,610,033 | B1 | | 8/2003 | Melanson et al. |
| 6,638,244 | B1 | | 10/2003 | Reynolds |
| 6,645,171 | B1 | | 11/2003 | Robinson et al. |
| 6,645,181 | B1 | | 11/2003 | Lavi et al. |
| 6,689,108 | B2 | | 2/2004 | Lavi et al. |
| 6,746,438 | B1 | | 6/2004 | Arnissolle |
| 6,764,467 | B1 | | 7/2004 | Roby et al. |
| 2002/0022804 | A1 | | 2/2002 | Connolly et al. |
| 2003/0199832 | A1 | | 10/2003 | Greiner-Perth et al. |
| 2004/0059312 | A1 | | 3/2004 | Frezza et al. |
| 2004/0122359 | A1 | | 6/2004 | Wenz et al. |

FOREIGN PATENT DOCUMENTS

| | | |
|---|---|---|
| EP | 112574 | 7/1984 |
| EP | 268700 | 11/1986 |
| EP | 344956 | 12/1989 |
| FR | 2714824 | 7/1995 |
| FR | 2799654 | 4/2001 |
| FR | 2801220 | 5/2001 |
| FR | 2869795 | 11/2005 |
| GB | 1114238 | 5/1968 |
| GB | 1197712 | 7/1970 |
| WO | WO 02/072173 | 9/2002 |
| WO | WO 2007/101784 | 9/2007 |
| WO | WO 2007/101786 | 9/2007 |
| WO | WO 2007/101798 | 9/2007 |
| WO | WO 2007/122209 | 11/2007 |

OTHER PUBLICATIONS

International Search Report of PCT/EP07/051607, dated Jun. 15, 2007.

International Search Report of PCT/EP07/051115, dated Nov. 21, 2007.

DE 4314090 Machine Translation, published Nov. 3, 1994.

EP 268700 English Abstract, published Jun. 1, 1988.

EP 112574 English Abstract, published Jul. 4, 1984.

FR 2869795 English Abstract, published Nov. 11, 2005.

FR 2801220 English Abstract, published May 25, 2001.

FR 2799654 English Abstract, published Apr. 20, 2001.

Notice of Abandonment mailed Oct. 29, 2010 in U.S. Appl. No. 12/282,927, filed Oct. 28, 2008 by Radmer et al.

Non-Final Office Action mailed Mar. 25, 2010 in U.S. Appl. No. 12/281,533, filed Feb. 16, 2009 by Radmer et al.

Notice of Abandonment mailed Oct. 21, 2010 in U.S. Appl. No. 12/281,382, filed Dec. 17, 2008 by Radmer et al.

Notice of Abandonment mailed Oct. 21, 2010 in U.S. Appl. No. 12/218,533, filed Feb. 16, 2009 by Radmer et al.

* cited by examiner

ONE-HAND OPERATED DRUG MIXING AND EXPELLING DEVICE

CROSS-REFERENCE TO RELATED APPLICATIONS

This application is a 35 U.S.C. §371 national stage application of International Patent Application PCT/EP2007/055623 (published as WO 2007/147741), filed Jun. 7, 2007, which claimed priority of European Patent Applications 06115841.6, filed Jun. 21, 2006 and 06119143.3, filed Aug. 18, 2006; this application further claims priority under 35 U.S.C. §119 of U.S. Provisional Applications 60/816,049, filed Jun. 23, 2006 and 60/839,283, filed Aug. 22, 2006.

FIELD OF THE INVENTION

The present invention relates to a device for mixing and expelling a drug, in particularly for mixing a solid drug, such as a powdered or lyophilized drug, with a liquid, such as a solvent liquid, i.e. for reconstitution of the drug. In particular, the invention relates to a mixing and expelling device which can be operated by use of one hand only.

BACKGROUND OF THE INVENTION

It is still desirable to store a drug in powdered or lyophilized form and therefore necessary to reconstitute the drug before it is delivered to a person, i.e. it is necessary to mix the drug with a liquid, thereby forming a liquid drug. This is normally done by means of an ordinary syringe with an ordinary needle. Liquid is sucked into the syringe, the needle is then inserted in a vial containing the lyophilized drug to be reconstituted, and the liquid is forced from the syringe into the vial by means of a movable piston of the syringe. When the lyophilized drug has been properly reconstituted, the movable piston is pulled out, and the reconstituted drug is thereby retrieved to the syringe. The reconstituted drug may subsequently be delivered from the syringe to a person. The administration procedure involves a huge amount of steps making it complicated for the user, and there is a relatively high risk of contamination of the drug or the syringe during the described procedure due to the exposure of the surfaces and the needle to un-sterile free air and dirt.

Furthermore, it can be inconvenient and difficult for user to drag and pull the piston of the syringe, while simultaneously keeping control over the infusion needle from moving in and out of the vein, as both hands are needed for the administration kit.

Further, due to the nature of the disorders, some users have problems with delivering the necessary amount of holding and actuating force to process the administration.

Some of these problems are addressed in U.S. Pat. Nos. 6,764,467, 5,329,976, 4,738,660, 4,410,321, 6,645,171 and FR 2714824.

SUMMARY OF THE INVENTION

It is an object of the present invention to provide a device for reconstituting a drug in which the risk of contamination during the process is minimised.

It is a further object of the invention to provide a device for reconstituting a drug, which is easier for the user to operate during reconstitution, aspiration and infusion.

It is an even further object of the invention to provide a device for reconstituting a drug, which requires minimal forces to operate by the user.

The above objects and other objects are achieved by the drug mixing and expelling device according to the invention, said drug mixing and expelling device comprising:

- a reservoir containing a liquid,
- a vial containing a drug,
- means for establishing a fluid connection between the reservoir and the vial and for establishing fluid connection between the vial and an infusion outlet,
- means for forcing the liquid from the reservoir to the vial via an established fluid connection, and
- means for activating said forcing means during establishment of said fluid connection between the reservoir and the vial.

The drug mixing and expelling device is preferably a disposable device, wherein the reservoir, the vial, the means for establishing said fluid connections, the forcing means and the means for activating form an at least substantially integral device.

In the present context the term ‘integral device’ should be interpreted to mean a device which is manufactured and operated as one device. The parts may, e.g., be at least substantially surrounded by a housing.

The reservoir may be any suitable kind of reservoir, such as a container, a vial, a syringe or a flexible reservoir forming a chamber in the device. The liquid contained in the reservoir is preferably a solvent liquid being suitable for reconstitution of a drug contained in the vial, such as a lyophilized drug. The amount and kind of liquid in the reservoir is chosen in such a manner that it matches a specific drug contained in the vial. Thereby it is ensured that the drug is reconstituted correctly and in a suitable manner by use of only one single integral device.

A vial adapter may form a part of the device and is shaped in such a manner that the vial is positioned there in a manner which substantially fixes the vial in the device.

By integrating the liquid and the drug in one sterile device, it is possible to avoid the majority of contamination risks from open endings during mounting and dismounting of parts during the reconstitution process. Likewise, by needing only one device to process the administration, it is possible to both minimise the amount of steps and to make the full administration less complicated for the user.

The means for establishing the fluid connection may comprise a first spike adapted to penetrate a septum of the vial, e.g. positioned in the vial adapter. The first spike is preferably a hollow spike, the hollow part thereby giving access to the interior of the vial once the first spike has penetrated the septum.

The means for establishing the fluid connection may further comprise a second spike adapted to penetrate the reservoir. The second spike is also preferably a hollow spike, the hollow part thereby giving access to the interior of the reservoir once the second spike has penetrated the reservoir. The first and second spikes may advantageously form part of a double pointed hollow needle. In this case the first spike will penetrate the septum of the vial and the second spike will penetrate the septum of the reservoir, and the hollow portion of the double pointed hollow needle will thereby establish a fluid connection between the reservoir and the vial.

Alternatively or additionally, the means for establishing the fluid connection may comprise a valve system for opening and closing the fluid connection between the vial and reservoir. The valve may e.g. be used in connection with the first spike, so that the septum of the vial is penetrated by the first spike while the fluid connection to the reservoir is provided by opening the valve and not by penetration of a septum.

The forcing means may comprise a movable piston (or plunger) positioned in the reservoir in such a manner that the liquid is forced out of the reservoir and into the vial when the piston is moved in a specified direction. The forcing means is preferably driven by a spring preloaded with accumulated energy stored, but it may be pneumatic driven, such as by a gas cylinder, and/or electrical driven and/or driven by a gas generation resulting from a chemical process and/or by expanding material(s) i.e. with latent energy stored in the chemical substance.

The force acting on the piston may be adapted to move the liquid reservoir towards the vial for establishing the fluid connection. The reservoir may e.g. be moved towards the second spike for penetrating the septum and subsequently the piston is moved further for forcing liquid from the reservoir into the vial via the fluid connection which has been established between the reservoir and the vial. Thereby the drug contained in the vial will be reconstituted in the vial.

The force acting on the forcing means is sufficient to overcome the pressure provided in the vial due to the liquid forced therein and thereby to keep the piston in an end position in which the liquid is forced into the vial. Thus, it is possible for the user to monitor a proper mixture of the reconstituted drug in the vial, as the holding force, e.g. from the spring, keeps the piston in an end position, wherein the liquid is maintained in the vial.

The pressure in the vial may subsequently be used for automatic infusion of the drug via a butterfly needle connected to the infusion outlet. Alternatively, a syringe can be connected to the infusion outlet, and the reconstituted drug will automatically be transferred to the syringe due to the pressure build up in the vial. In any case, the device is capable of not only mixing but also expelling of the drug. If for some reason there still remains drug in the vial, the plunger of the syringe can be pulled further back to suck the remaining drug into the syringe.

The activating means is adapted to activate the forcing means during establishment of the fluid connection between the vial and reservoir, such as during pressing the vial towards the first spike for penetrating the septum.

The activating means may comprise one or more rods or other pushing means provided in the device, which are adapted to activate/release the forcing means upon by being pushed. For example by moving the vial towards the first spike for penetrating the septum of the vial, the rod may be moved and the forcing means is activated subsequently, which results in a movement of the piston. The activating means may be connected direct to the forcing means and/or to the liquid reservoir. In the latter case, the liquid reservoir will be pre-biased before the forcing means is activated.

If a septum of the reservoir has not been penetrated yet, the piston will move the reservoir towards the second spike, and when the second spike has penetrated the septum of the reservoir the liquid is forced into the vial during further movement of the piston.

However, in another embodiment, the reservoir may be sealed/closed by other means than a septum, e.g. a valve system, which may be activated e.g. in response to the movement of the vial towards the first spike, and the piston will then force the liquid into the vial when the valve system has opened the fluid connection.

The abovementioned rod(s) may either be connected directly to the forcing means or interact with other mechanisms for activating/releasing the forcing means.

The device allows for infusion directly from the vial after reconstitution of the drug, as the pressure provided in the vial during forcing the liquid into the vial is used to infuse the drug. A valve may be provided for opening and closing the fluid connection between the vial and the infusion outlet for controlling the flow rate. Said valve may be a variable flow controlled valve, e.g. a needle valve, for adjusting the flow rate from the vial.

By having a spring-loaded piston in the reservoir which is activated by the same force used to penetrate the septum of the vial, the needed force for reconstitution is reduced to a minimum. The force applied by the spring is used i.a. to the following steps without the need of any additional applied forces:

- pressing liquid into the vial to reconstitute the drug,
- acting as a holding force for the piston, making it possible for the user to monitor a proper mixture of the reconstituted solution, and
- infusion or transferring the reconstituted drug to another reservoir (e.g. a syringe) by means of the pressure built up in the vial by the process of pressing the liquid into the vial.

The user needs to aspirate before infusion, and the device may therefore also comprise a suction unit. The suction unit may be provided at a location between said vial and the infusion outlet for aspirating.

The suction unit may comprise a syringe with a syringe plunge rod, which may be a one-way syringe only allowing its piston to move in the suction direction in order to avoid infusion of air into the vein.

In another embodiment, the suction unit may comprise a syringe having an air permeable membrane.

In another embodiment, the suction unit may comprise a pump with an inlet and outlet tube connected on opposite sides of said valve, respectively, said inlet and outlet tubes each comprising a one-way valve. The pump may be manually or electrically driven or driven by the force provided by the spring acting on the piston, as described above.

In another embodiment, the suction unit may be connected to a chamber provided on an opposite side of the piston in relation to the liquid in the reservoir, so that a suction process is provided through the unit, when said piston forces the liquid into the vial. Thus, the movement of the piston in the reservoir is used both for reconstitution and aspiration.

Preferably, the suction unit forms part of the integral device.

This invention provides an 'all-in-one' and/or a 'ready-to-use' package which is easy to operate for the user, as it can be operate by one hand only, which then gives the user a free hand to handle the butterfly needle. It is only necessary to press the vial towards the first spike, as the forcing means then automatically will cause the liquid from the reservoir to enter the vial in order to cause reconstitution of the drug. When the liquid has entered the vial, the user may aspirate and then infuse the drug from the vial by use of the pressure provided in the vial.

Thus, the invention provides the user with a device having a very low actuating force for the reconstitution process, an automatic reconstitution, automatic infusion, fewer numbers of steps, more convenient to use, reduce the risk of contamination and makes it possible to reconstitute, aspirate and infuse by use of only one hand. The other hand can then be used for other purposes during the administration, e.g. controlling the butterfly needle in the vein.

Furthermore, as the vial and reservoir is provided in the same device, preferably being disposable, it is ensured that the amount and kind of liquid in the reservoir matches the drug of a specific kind of vial. Thereby the risk of incorrect reconstitution of the drug is reduced.

FEATURES OF THE INVENTION

1. A drug mixing and expelling device comprising:
   a reservoir containing a liquid,
   a vial containing a drug,
   means for establishing a fluid connection between the reservoir and the vial and for establishing fluid connection between the vial and an infusion outlet,
   integrated forcing means with accumulated or latent energy stored for forcing the liquid from the reservoir to the vial via an established fluid connection, and
   activating means for activating said integrated forcing means upon establishment of said fluid connection between the reservoir and the vial.
2. A drug mixing and expelling device according to feature 1, wherein the reservoir for liquid, the vial, the means for establishing said fluid connections, the forcing means and the means for activating form an integral device.
3. A drug mixing and expelling device according to feature 1 or 2, wherein the means for establishing a fluid connection comprises a first spike adapted to penetrate a septum of the vial.
4. A drug mixing and expelling device according to any of features 1-3, wherein the means for establishing a fluid connection further comprises a second spike adapted to penetrate a septum of the reservoir.
5. A drug mixing and expelling device according to any of features 1-4, wherein said activating means is adapted to activate the forcing means during pressing the vial towards the first spike for penetrating the septum.
6. A drug mixing and expelling device according to any of features 1-5, wherein the means for establishing a fluid connection comprises a valve system for opening and closing a fluid connection between the vial and reservoir.
7. A drug mixing and expelling device according to any of features 1-6, wherein the means for forcing comprise a piston or plunger provided in the reservoir and adapted to force the liquid into the vial.
8. A drug mixing and expelling device according to feature 7, wherein the piston or plunger is driven by a spring and/or is pneumatic driven and/or is electrical driven and/or driven by a gas and/or by an expanding material, the force acting on the piston or plunger being adapted to keep the piston or plunger in an end position in which the liquid has been forced into the vial.
9. A drug mixing and expelling device according to feature 7 or 8, wherein the force acting on the piston or plunger is adapted to move the liquid reservoir towards the vial for establishing the fluid connection.
10. A drug mixing and expelling device according to any of the preceding features, wherein a valve is provided for opening and closing the fluid connection between the vial and the infusion outlet for controlling the flow rate.
11. A drug mixing and expelling device according to feature 10, wherein the valve is a variable flow controlled valve.
12. A drug mixing and expelling device according to any of the preceding features, wherein a suction unit is provided at a location between said vial and the infusion outlet for aspirating.
13. A drug mixing and expelling device according to feature 12, wherein the suction unit comprises a syringe with a syringe plunger rod.
14. A drug mixing and expelling device according to feature 13, wherein the syringe is a one-way syringe only allowing its piston to move in the suction direction.
15. A drug mixing and expelling device according to feature 12, wherein the suction unit comprises syringe having an air permeable membrane.
16. A drug mixing and expelling device according to feature 10 or 11, and comprising a suction unit that comprises a pump with an inlet and outlet tube connected on opposite sides of said valve, respectively, said inlet and outlet tubes each comprising a one-way valve.
17. A drug mixing and expelling device according to feature 16, wherein the pump is manually or electrically driven or driven by the force provided by the spring acting on the piston.
18. A drug mixing and expelling device according to feature 12, wherein the suction unit is connected to a chamber provided on an opposite side of the piston or plunger in relation to the liquid in the reservoir, so that a suction process is provided through the suction unit, when said piston forces the liquid into the vial.
19. A drug mixing and expelling device according to feature 12, wherein the suction unit forms part of the integral device of feature 2.

BRIEF DESCRIPTION OF THE DRAWINGS

The invention will now be described in further details below with reference to the accompanying drawings in which.

DETAILED DESCRIPTION OF THE DRAWINGS

Figure 1:
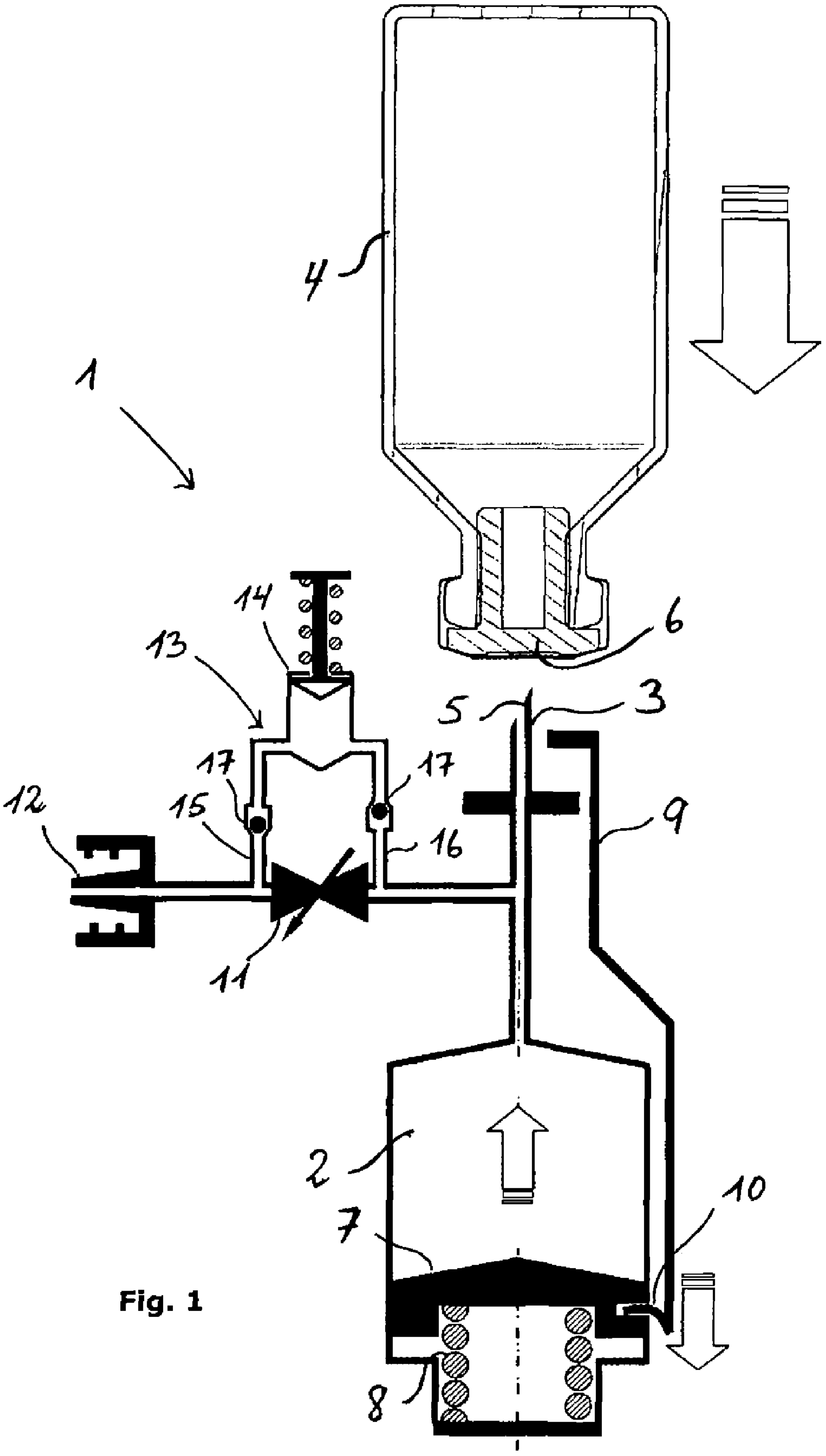
FIG. 1 shows a principal sketch of a first embodiment of the drug mixing and expelling device according to the invention.

FIG. 1 shows a principal sketch of a first embodiment of the drug mixing and expelling device according to the invention. The device 1 comprises a reservoir 2 containing a liquid and a vial adapter 3 for receiving a vial 4 containing a drug. At the vial adapter 3 there is positioned a first hollow spike 5 adapted to penetrate a septum 6 of the vial 4. A movable piston 7 is positioned in the reservoir 2 and is spring-loaded by a spring 8. When the vial is pressed towards the first hollow spike 5 for penetrating the septum 6, the vial 4 engages activating means in the form of a rod 9, which releases the release mechanism 10 that holds the piston in the pre-loaded position of FIG. 1.

The piston 7 is movable inside the reservoir 2 in an upwards direction. Thereby the piston 7 forces liquid from the reservoir 2 through the fluid connection provided by the hollow spike 5 and into the vial 4. Thereby the drug in the vial 4 is reconstituted. The force of the spring 8 is high enough to overcome the pressure in the vial 4 and thus to keep the piston 7 in an end position wherein the liquid is forced into the vial 4.

The reconstituted drug can be infused directly from the vial due to the pressure in the vial. A valve 11 is provided for opening and closing the fluid connection between the vial 4 and the infusion outlet 12, so as to control the flow rate from the vial 4. The infusion outlet 12 may be coupled to a butterfly infusion needle.

A suction unit 13 is provided at the fluid connection between the infusion outlet 12 and vial 4 for aspiration. The suction unit 13 comprises a manually operated pump 14 with an inlet and outlet tube 15, 16 connected on opposite sides of said valve 11, respectively, the inlet and outlet tubes each comprising a one-way valve 17. Thus, air and blood can be aspirated through the inlet tube 15 and into the vial before infusing the drug.

The device 1 comprises a housing (not shown) surrounding the parts shown in FIG. 1.

Figure 2A:
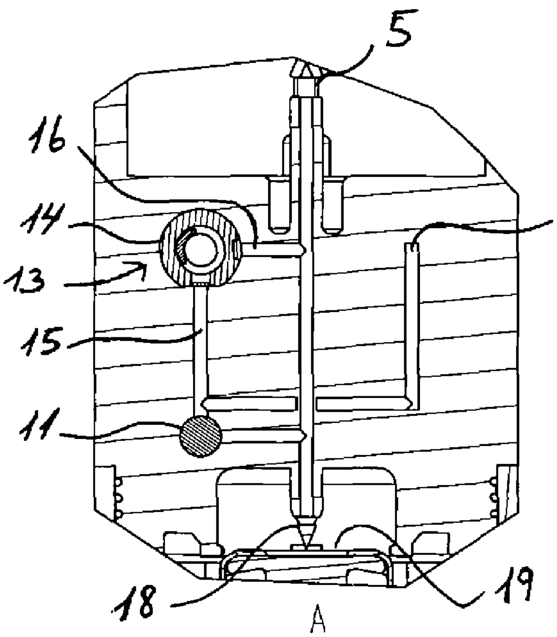
FIG. 2*a-c* show cross-sectional views of another embodiment of the device according to the invention.
Figure 2B:
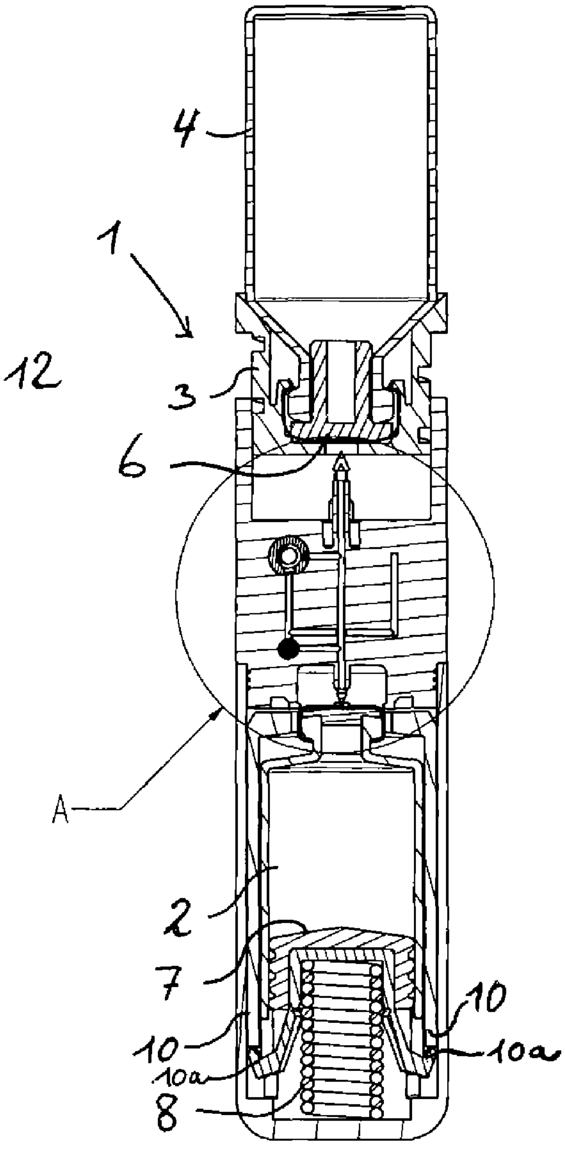
Figure 2C:
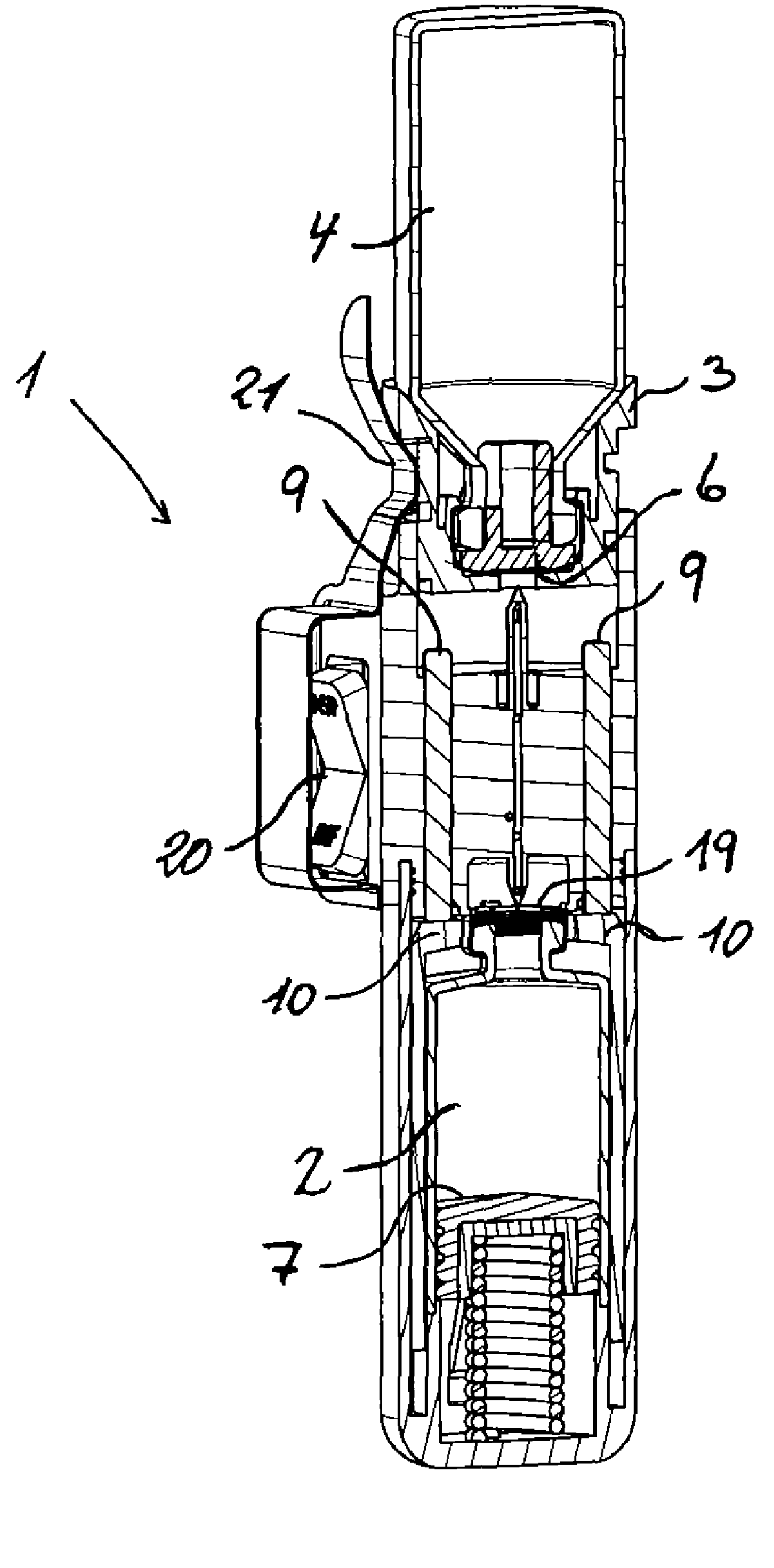

FIGS. 2*a-c* show cross-sectional views of another embodiment of the device according to the invention. The device 1 comprises a reservoir 2 and a vial 4 positioned in the vial adapter 3. Neither the septum 6 of the vial, nor the septum 19 of the reservoir has been penetrated by the first spike 5 and the second spike 18, respectively. Thus, there is no fluid connection between the reservoir 2 and the vial 4. In order to operate the device 1, the user presses the vial 4 in the direction towards the first spike 5. Thereby the first hollow spike 5 penetrates the septum 6 of the vial 4. Upon moving the vial 4 further on in the same direction, the vial adapter 3 engages the rods 9 which are pushed downwards and engage the release mechanism 10 that releases the taps 10*a* and thus the spring 8.

As the spring 8 is released, the piston 7 moves the reservoir 2 upwards towards the second spike 18 which penetrates the septum 19 of the reservoir. Thereby a fluid connection between the reservoir 2 and the vial 4 is established. The spring 8 now moves the piston 7 further and forces the liquid into the vial 4 via the established fluid connection, and the drug in the vial 4 is reconstituted.

A valve 11 opens and closes the fluid connection between the vial 4 and the infusion outlet 12, so as to adjust the infusion of drug coming directly from the vial 4.

A suction unit 13 is provided at the fluid connection between the infusion outlet 12 and vial 4. The suction unit 13 comprises a manually operated pump 14 with an inlet and outlet tube 15, 16 connected on opposite sides of said valve 11, respectively, the inlet and outlet tubes each comprising a one-way valve. Thus, air and blood can be aspirated through the inlet tube 15 and into the vial before infusing of the drug. The pump 14 and valve 11 is operated by a push-button 20.

A lever 21 is provided for engaging with a recess in the vial adapter 3, the lever 21 ensuring that the vial 4 is locked in a "stand by" position until the user presses it downwards.

Figure 3:
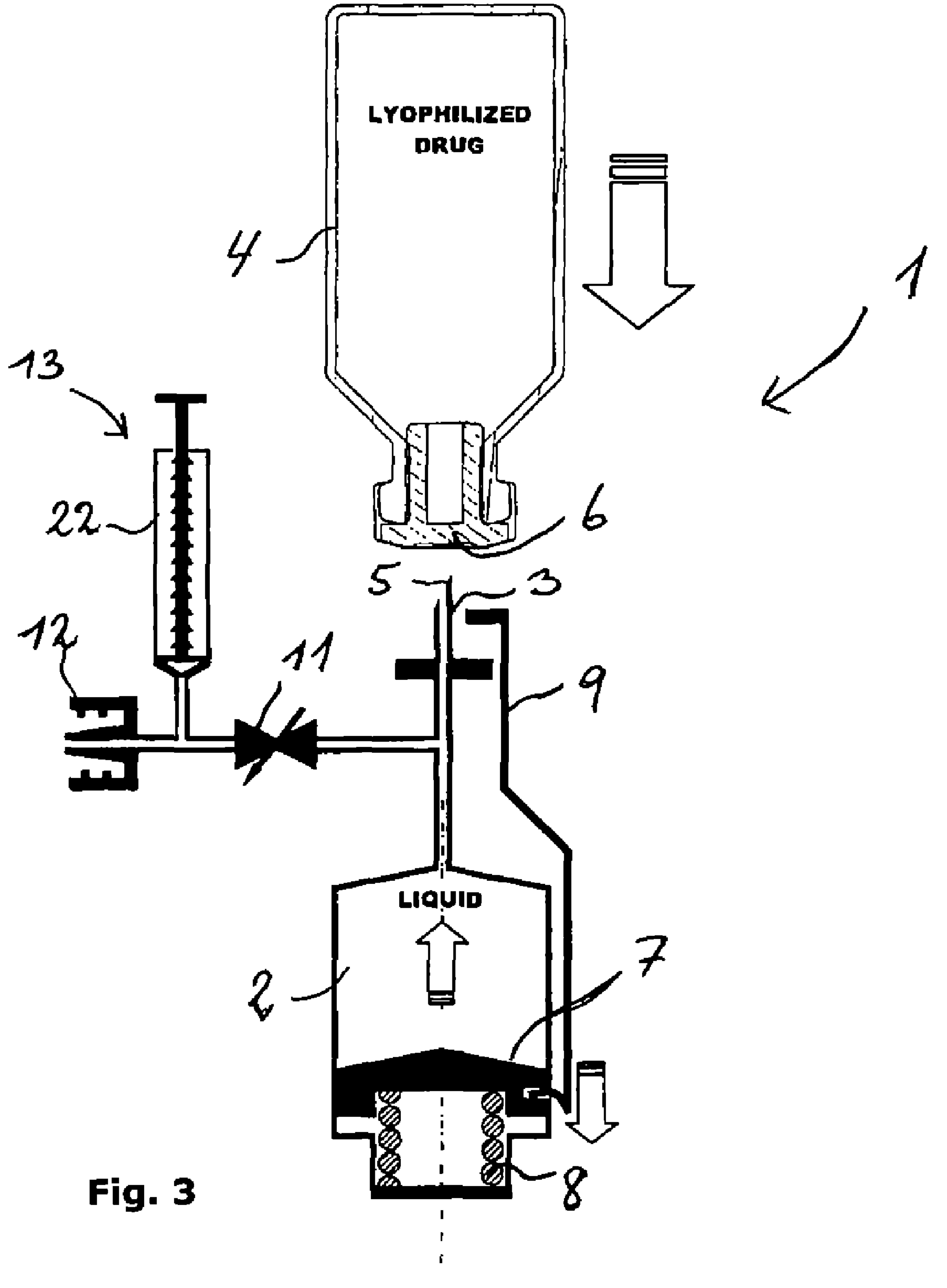
FIG. 3 shows a further embodiment of the drug mixing and expelling device according to the invention.

FIG. 3 shows another embodiment of the device according to the invention. The embodiment is similar to the embodiment shown in FIG. 1, except for the suction unit 13. The unit 13 of this embodiment comprises a syringe 22 which is a one-way syringe only allowing its piston to move in the suction direction and thereby avoids the risk of infusing air into the vein.

The device of FIG. 3 is operated as follows;

The vial 4 is pressed on the vial adapter 3 penetrating the septum 6 of the vial. Concurrently, the activation of the rod 9 is releasing the spring-loaded piston 7 which forces liquid into the vial 4 for reconstitution. The holding force from the spring 7 keeps the piston in an end position, wherein the liquid is maintained in the vial and thus makes it possible for the user to monitor a proper mixture of the reconstituted solution. Then a butterfly needle is coupled to the infusion outlet 12, and the aspiration is done by manually pulling the syringe plunger rod of the syringe 22. Then the infusion is started by turning the valve 11, and the infusion rate is controlled by adjusting the valve 11. Due to the pressure in the vial 4, the infusion will start and complete by its own force.

Figure 4:
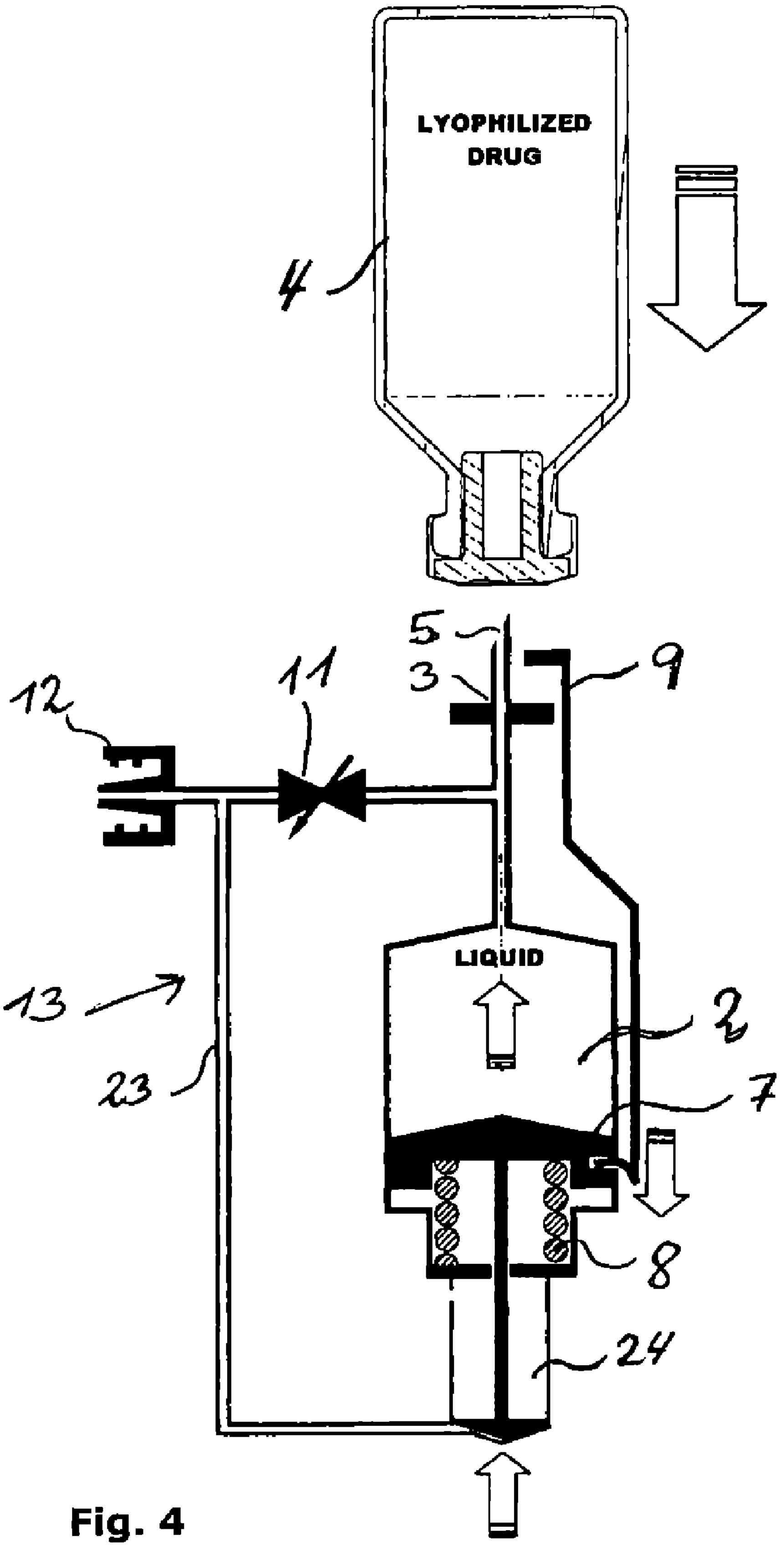
FIG. 4 shows a further embodiment of the drug mixing and expelling device according to the invention.

FIG. 4 shows a further embodiment of the device according to the invention. The embodiment is similar to the embodiment of FIGS. 1 and 3, except for the suction/aspiration unit 13. The suction unit 13 is connected via a tube 23 to a chamber 24 provided on an opposite side of the piston 7 in relation to the liquid in the reservoir 2, so that a suction process is provided through the unit 13, when said piston 7 forces the liquid into the vial 4. The principle is to use the force from the spring 8 to handle the aspiration and thus reducing the number of user handled steps by one.

Figure 5:
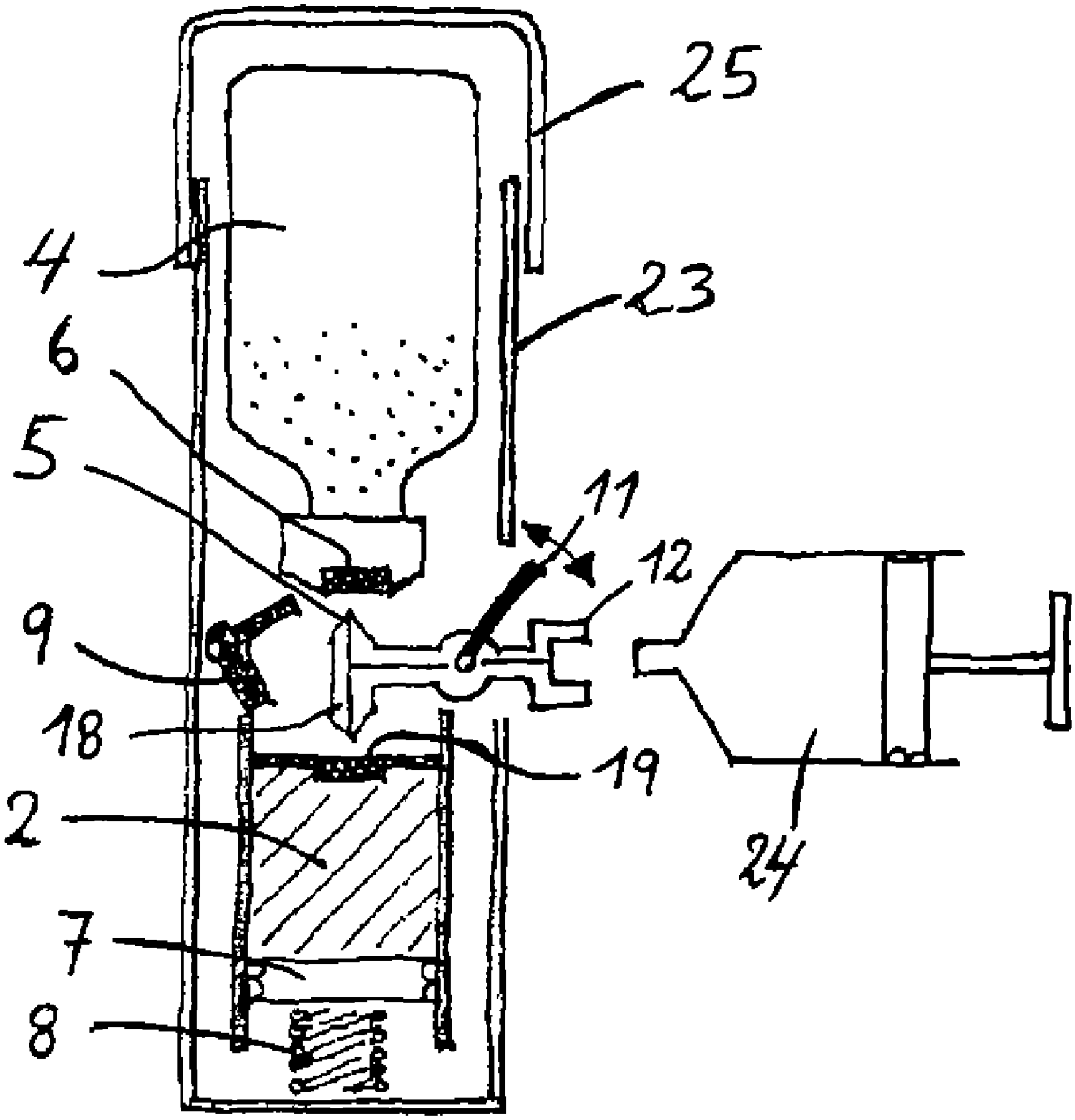
FIG. 5 shows a further embodiment of the drug mixing and expelling device according to the invention.

FIG. 5 shows a further embodiment of the device according to the invention. The vial 4 positioned in the housing 23 is pressed down, and the septum 6 is penetrated by the first spike 5. Concurrently, the activation of the release mechanism 9 is releasing the reservoir 2, which is moved upwards by the spring 8 acting on the plunger 7. The spring 8 together with the plunger 7 moves the reservoir 2 upwards towards the second spike 18 which penetrates the septum 19 of the reservoir. When the septum 19 is penetrated, a fluid connection between the vial 4 and reservoir 2 is established, and the liquid is forced into the vial 4 by the plunger 7 for reconstitution. The holding force from the spring 8 keeps the plunger 7 in an end position, wherein the liquid is maintained in the vial 4 and thus makes it possible for the user to monitor a proper mixture of the reconstituted solution. The housing 23 may have transparent areas allowing inspection of the reconstitution process.

A syringe 24 (or a butterfly needle) is attached to the outlet 12, and the valve 11 is then turned so as to open the fluid connection between the outlet 12 and the vial 4, whereby the reconstituted drug is forced into the syringe by the pressure built up in the vial 4.

The housing 23 comprises a cap 25, which is slidably engaged with the other part of the housing, so that the user can press on said cap 25 for pressing the vial 4 towards the first spike 5. The cap 25 may also protect the vial 4 from unintentional activation. The spikes 5, 18, the valve 11 and the outlet 12 are preferably fixed to the housing 23.

To prevent a situation where the valve 11 is open when the vial 4 is pushed down with subsequent waste of drug, a mechanical interlock between the handle of the valve 11 and the vial's position may be provided. Another interlock between the valve 11 and the syringe 24 may be provided to prevent the opening to the outlet 12 without having the syringe 24 attached thereto. This could be achieved for example with a special built valve that opens when the syringe 24 is connected to the outlet 12.

The invention claimed is:

1. A drug mixing and expelling device comprising:

a reservoir containing a liquid, a vial having a non-movable solid bottom and containing a drug, means for establishing a fluid connection between the reservoir and the vial and for establishing fluid connection between the vial and an infusion outlet, integrated forcing means with accumulated or latent energy stored for forcing the liquid from the reservoir to the vial via an established fluid connection, and activating means for activating said integrated forcing means upon establishment of said fluid connection between the reservoir and the vial.

2. A drug mixing and expelling device according to claim 1, wherein the reservoir for liquid, the vial, the means for establishing said fluid connections, the forcing means and the means for activating form an integral device.

3. A drug mixing and expelling device according to claim 1, wherein the means for establishing a fluid connection comprises a first spike adapted to penetrate a septum of the vial.

4. A drug mixing and expelling device according to claim 3, wherein the means for establishing a fluid connection further comprises a second spike adapted to penetrate a septum of the reservoir.

5. A drug mixing and expelling device according to claim 1, wherein said activating means is adapted to activate the forcing means during pressing the vial towards the first spike for penetrating the septum.

6. A drug mixing and expelling device according to claim 1, wherein the means for establishing a fluid connection comprises a valve system for opening and closing a fluid connection between the vial and reservoir.

7. A drug mixing and expelling device according to claim 1, wherein the forcing means comprises a piston or plunger provided in the reservoir and adapted to force the liquid into the vial.

8. A drug mixing and expelling device according to claim 7, wherein the piston or plunger is at least one of spring driven, pneumatic driven, electrically driven, gas driven or expanding material driven, the force acting on the piston or plunger being adapted to keep the piston or plunger in an end position in which the liquid has been forced into the vial.

9. A drug mixing and expelling device according to claim 7, wherein the force acting on the piston or plunger is adapted to move the liquid reservoir towards the vial for establishing the fluid connection.

10. A drug mixing and expelling device according to claim 1, wherein a valve is provided for opening and closing the fluid connection between the vial and the infusion outlet for controlling the flow rate.

11. A drug mixing and expelling device according to claim 10, wherein the valve is a variable flow controlled valve.

12. A drug mixing and expelling device according to claim 10, and comprising a suction unit that comprises a pump with an inlet and outlet tube connected on opposite sides of said valve, respectively, said inlet and outlet tubes each comprising a one-way valve.

13. A drug mixing and expelling device according to claim 12, wherein the pump is manually or electrically driven or driven by the force provided by the spring acting on the piston.

14. A drug mixing and expelling device according to claim 1, wherein a suction unit is provided at a location between said vial and the infusion outlet for aspirating.

15. A drug mixing and expelling device according to claim 14, wherein the suction unit comprises a syringe with a syringe plunger rod.

16. A drug mixing and expelling device according to claim 15, wherein the syringe is a one-way syringe only allowing its piston to move in the suction direction.

17. A drug mixing and expelling device according to claim 14, wherein the suction unit comprises syringe having an air permeable membrane.

18. A drug mixing and expelling device according to claim 14, wherein the suction unit is connected to a chamber provided on an opposite side of the piston or plunger in relation to the liquid in the reservoir, so that a suction process is provided through the suction unit, when said piston forces the liquid into the vial.

19. A drug mixing and expelling device according to claim 14, wherein the reservoir for liquid, the vial, the means for establishing said fluid connections, the forcing means and the means for activating the suction unit form an integral device.

20. A drug mixing and expelling device comprising: a reservoir containing a liquid, a vial having a drug containing compartment of fixed volume and having a non-movable solid bottom, means for establishing a fluid connection between the reservoir and the vial and for establishing fluid connection between the vial and an infusion outlet, integrated forcing means with accumulated or latent energy stored for forcing the liquid from the reservoir to the vial via an established fluid connection, and activating means for activating said integrated forcing means upon establishment of said fluid connection between the reservoir and the vial.

* * * * *